United States Patent [19]

Lind

[11] 4,066,616

[45] Jan. 3, 1978

[54] HYDROXYARYL HYDANTOINS AND THEIR USE AS STABILIZERS

[75] Inventor: Hanns Lind, Liestal, Switzerland

[73] Assignee: Ciba-Geigy Corporation, Ardsley, N.Y.

[21] Appl. No.: 664,451

[22] Filed: Mar. 8, 1976

Related U.S. Application Data

[62] Division of Ser. No. 452,763, March 19, 1974, Pat. No. 3,956,298.

[51] Int. Cl.² ............... C07D 233/78; C08K 5/34
[52] U.S. Cl. .................. 260/45.8 NT; 106/176; 260/75 N; 548/307
[58] Field of Search ............ 260/45.8 NB, 309.5

[56] References Cited

U.S. PATENT DOCUMENTS

| | | | |
|---|---|---|---|
| 3,734,926 | 5/1973 | Dexter | 260/45.8 NB |
| 3,746,721 | 7/1973 | Stephen | 260/45.8 NB |
| 3,882,137 | 5/1975 | Habermeier et al. | 260/309.5 |
| 3,919,234 | 11/1975 | Ramey et al. | 260/45.8 NB |
| 3,939,175 | 2/1976 | Schmidt et al. | 260/309.5 |
| 4,001,299 | 1/1977 | Dexter et al. | 260/45.8 NB |

*Primary Examiner*—Donald E. Czaja
*Assistant Examiner*—R. A. White
*Attorney, Agent, or Firm*—Nestor W. Shust

[57] ABSTRACT

The new N-[3-(3-hydroxyaryl)-2-hydroxypropyl]-imides may be prepared by reacting 3-(3-hydroxyaryl)-propenoxides with cyclic imides. These hydroxy compounds as well as their esters with carboxylic acids are highly effective in the stabilization of polymers, preferably of polyolefins, against thermal-oxydative attack. The compounds themselves exhibit a good stability against discoloration by radiation or gas fading.

10 Claims, No Drawings

HYDROXYARYL HYDANTOINS AND THEIR USE AS STABILIZERS

This is a divisional of applicatin Ser. No. 452,763, filed on Mar. 19, 1974, now U.S. Pat. No. 3,956,298.

The present invention relates to new derivatives of cyclic imides, a process for their manufacture, their use as stabilisers for organic polymers and stabilised polymer compositions which contain these new compounds.

The subject of the invention are compounds of the formula I

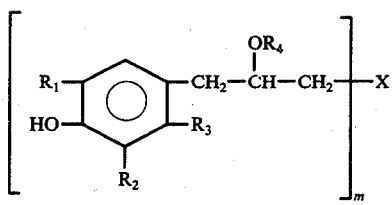
(I)

wherein $m$ is an integer from 1 to 3 and $R_1$ denotes an alkyl group with 1 to 8 carbon atoms, a cycloalkyl group with 6 to 8 carbon atoms or an aralkyl group with 7 to 9 carbon atoms, $R_2$ denotes hydrogen, an alkyl group with 1 to 8 carbon atoms, a cycloalkyl group with 6 to 8 carbon atoms or an aralkyl group with 7 to 9 carbon atoms, $R_3$ denotes hydrogen or a methyl group, $R_4$ denotes hydrogen or a

group, $R_5$, if $m = 1$ to 3, denotes an alkyl group with 1 to 17 carbon atoms, a cyclohexyl group, a phenyl group or substituted phenyl group, or an aralkyl group which can be substituted by alkyl and/or hydroxyl groups in the aromatic radical, or, if $m = 1$, denotes a group

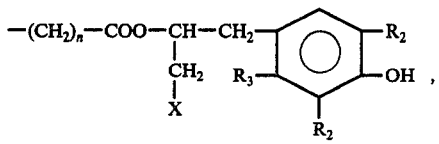

X denotes the radical of a cyclic imide which is linked to the remainder of the molecule via $m$ imide nitrogen atoms and $n$ denotes an integer from 2 to 8.

If $R_1$ or $R_2$ denotes an alkyl group with 1 to 8 carbon atoms, this can be, for example, a methyl, ethyl, propyl, isopropyl, butyl, sec.-butyl, tert.-butyl, sec.-pentyl, tert.-pentyl, 2-ethylbutyl, 2-ethylhexyl, hexyl or 1,1,3,3-tetramethylbutyl group.

If $R_1$ or $R_2$ denotes a cycloalkyl group or an aralkyl group, this can be, for example, a cyclohexyl, methylcyclohexyl, dimethylcyclohexyl, benzyl, α-methylbenzyl or α, α-dimethylbenzyl group.

If $R_5$, in accordance with the definition, represents an alkyl group with 1 to 17 carbon atoms, this can be, for example, a methyl, ethyl, propyl, isobutyl, pentyl, 2-ethylhexyl, undecyl or heptadecyl group. When $R_5$ denotes a substituted phenyl group, this can be, for example, a chlorophenyl, dichlorophenyl, hydroxyphenyl, tolyl, xylyl, tertiary butylphenyl, dodecylphenyl, dimethyl-hydroxyphenyl, di-tert.-butyl-hydroxyphenyl, methoxyphenyl, isopropoxyphenyl or octadecyloxyphenyl group.

When $R_5$ denotes an aralkyl group which can be substituted by alkyl and/or hydroxyl groups in the aromatic radical, it can be, for example, a benzyl, phenethyl, phenylpropyl, hydroxybenzyl, di-isopropyl-hydroxybenzyl, 2-di-tert.-butyl-hydroxyphenylethyl, dimethylbenzyl or n-butylphenylpropyl group.

The radical X contains, according to the definition, at least one imide grouping

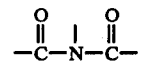

in a ring system. Ring systems with 2 or 3 imide groupings are preferred. Examples of suitable monoimide radicals X are the succinimide, maleimide, glutarimide, phthalimide, uric acid, hydantoin or 5,5-dimethylhydantoin radical, in which cases the index $m$ in the formula I denotes the number 1. Examples of diimide radicals are above all radicals of 5,5-dialkylbarbituric acids, such as 5,5-diethylbarbituric acid, radicals of alkylidene-bishydantoins, such as 5,5,5',5'-tetramethyl-1,1'-methylene- or -1,1'-tetramethylene- or 1,1'-octamethylene-bis-hydantoin, the uric acid radical or the pyromellitimide radical. In these cases, $m$ is the number 2. Amongst triimide radicals, the isocyanuric acid radical, in which $m$ denotes the number 3, should be mentioned above all.

Preferred compounds are those of the formula I wherein $R_1$ and $R_2$ independently of one another denote an alkyl group with 1 to 8 carbon atoms, $R_3$ denotes hydrogen, $R_4$ denotes hydrogen or a

group, $R_5$, if $m = 1$ to 3, denotes an alkyl group with 1 to 17 carbon atoms, a cyclohexyl group, a phenyl group, a phenyl group substituted by halogen, hydroxyl groups, alkyl groups with 1 to 4 carbon atoms or alkoxy groups with 1 to 18 carbon atoms, or a benzyl or phenethyl group substituted in the phenyl radical by one or two alkyl groups with 1 to 4 carbon atoms and/or a hydroxyl group, or, if $m = 1$, denotes a group

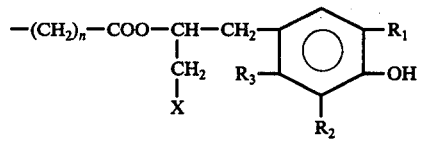

and X, $m$ and $n$ have the abovementioned meaning.

Compounds of particular interest are those of the formula I wherein $R_1$ and $R_2$ independently of one another denote an alkyl group with 1 to 4 carbon atoms, $R_3$ denotes hydrogen, $R_4$ denotes hydrogen or a

group, $R_5$, if $m = 1$ to 3, denotes an alkyl group with 1 to 17 carbon atoms or a

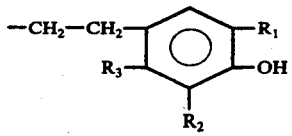

group or, if $m = 1$, denotes a

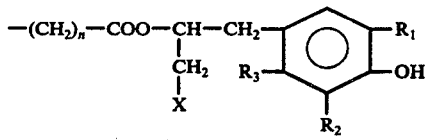

group and $n$ denotes an integer from 2 to 6 and X and $m$ have the abovementioned meaning, but above all those compounds of the formula I in which $R_1$ and $R_2$ independently of one another denote an alkyl group with 1 to 4 carbon atoms, but very particularly a tertiary butyl group, and $R_3$ and $R_4$ denote hydrogen, and X is the radical of a cyclic imide which is linked via 2 to 3 imide nitrogen atoms to the remainder of the molecule. These preferred compounds correspond to the formula

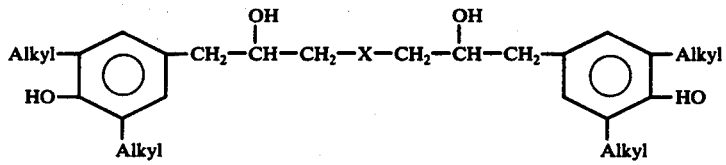

or the formula

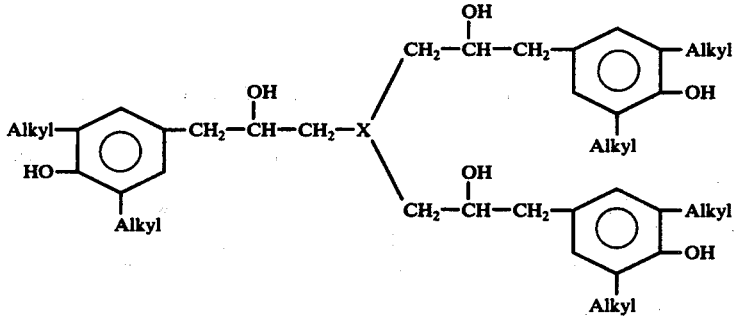

Herein, X in particular represents a radical of the formula

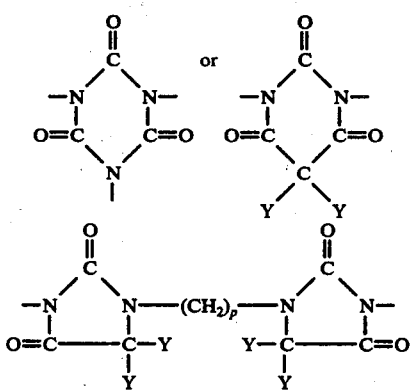

wherein Y denotes an alkyl group with 1 to 4 carbon atoms and $p$ denotes an integer from 1 to 8.

Examples of specific compounds of the formula I are: N-[2-hydroxy-3-(3-methyl-5-tert.-butyl-4-hydroxyphenyl)-propyl]-phthalimide, N-[2-hydroxy-3-(3,5-di-tert.-butyl-4-hydroxyphenyl)-propyl]-glutarimide, N-[2-propionoxy-3-(3,5-di-tert.-butyl-4-hydroxyphenyl)-propyl]-glutarimide, N-[2-hydroxy-3-(3-methyl-5-tert.-butyl-4-hydroxyphenyl)-propyl]-maleimide, N-[2-acetoxy-3-(3-methyl-5-tert.-butyl-4-hydroxyphenyl)-propyl]-maleimide, N-[2-hydroxy-3-(3-tert.-butyl-4-hydroxyphenyl)-propyl]-tetrahydrophthalimide, N-[2-hydroxy-3-(3-tert.-butyl-4-hydroxyphenyl)-propyl]-4-nitrophthalimide, 3-[2-hydroxy-3-(3,5-di-tert.-octyl-4-hydroxyphenyl)-propyl]-5,5-dimethylhydantoin, N-[2-benzoyloxy-3-(3-dimethylbenzyl-4-hydroxyphenyl)-propyl]-succinimide, N-[2-hydroxy-3-(2,5-dimethyl-4-hydroxyphenyl)-propyl]-succinimide, 3,3'-bis-[2-hydroxy-3-(3-methyl-5-tert.-butyl-4-hydroxyphenyl)-propyl]5,5,5',5'-tetramethyl-1,1'-methylene-bis-hydantoin, 3,3'-bis-[2-hydroxy-3-(3,5-dimethyl-4-hydroxyphenyl)-propyl]-5,5,5',5'-tetramethyl-1,1'-methylene-bis-hydantoin, 3,3'-bis-[2-hydroxy-3-(3,5-di-tert.-butyl-4-hydroxyphenyl)-propyl]-5,5,5',5'-tetramethyl-1,1'-(1,4-butylene)-bis-hydantoin, 3,3'-bis-[2-hydroxy-3-(3,5-di-tert.-butyl-4-hydroxyphezyl)-propyl]-5,5,5',5'-tetramethyl-1,1'-(1,8-octylene)-bis-hydantoin, bis-[2-hydroxy-3-(3,5-di-tert.-butyl-4-hydroxyphenyl)-propyl]-5,5-dimethylbarbiturate, bis-[2-hydroxy-3-(3,5-di-tert.-butyl-4-hydroxyphenyl)-propyl]-5,5-diethylbarbiturate, bis-[2-hydroxy-3-(3-methyl-5-tert.-butyl-4-hydroxyphenyl)-propyl]-5,5-diethylbarbiturate, bis-[2-hydroxy-3-(3,5-dimethyl-4-hydroxyphenyl)propyl]-5,5-diethylbarbiturate, tris-[2-hydroxy-3-(3-methyl-5-tert.-butyl-4-hydroxyphenyl)-propyl]-isocyanurate, tris-[2-hydroxy-3-(3,5-di-tert.-butyl-4-hydroxyphenyl)-propyl]-isocyanurate, tris-[2-hydroxy-3-(3,5-di-isopropyl-4-hydroxyphenyl)-propyl]-isocyanurate and tris-[2-hydroxy-3-(3,5-dimethyl-4-hydroxyphenyl)-propyl]-isocyanurate.

The compounds according to the invention, of the formula I, can be obtained by reacting 4-hydroxypenzyl-oxiranes of the formula II

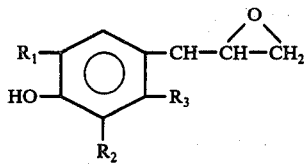

wherein $R_1$ denotes an alkyl group with 1 to 8 carbon atoms, a cycloalkyl group with 6 to 8 carbon atoms or an aralkyl group with 7 to 9 carbon atoms, $R_2$ denotes hydrogen, an alkyl group with 1 to 8 carbon atoms, a cycloalkyl group with 6 to 8 carbon atoms or an aralkyl group with 7 to 9 carbon atoms and $R_3$ denotes hydrogen or a methyl group, with a cyclic imide which possesses $m$ reactive imide nitrogen atoms, to give compounds of the formula III

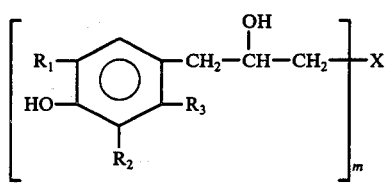

wherein $R_1$, $R_2$ and $R_3$ have the above mentioned meaning and X denotes the radical of a cyclic imide which is linked via $m$ imide nitrogen atoms to the remainder of the molecule, and $m$ denotes an integer from 1 to 3, and optionally subsequently reacting these compounds either (a) with at least $m$ mols of a compound of the formula

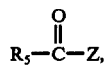

wherein $R_5$ denotes an alkyl group with 1 to 17 carbon atoms, a phenyl group or substituted phenyl group, or an aralkyl group which can be substituted by alkyl and/or hydroxyl groups in the aromatic radical, and Z denotes halogen, —OH or -O-alkyl with 1 to 4 carbon atoms in the alkyl radical, or with at least $m$ mols of a compound of the formula $(R_5CO)_2O$, wherein $R_5$ has the abovementioned meaning, or (b) if $m = 1$, with approximately 0.5 mol of a compound of the formula

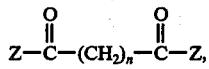

wherein $n$ denotes an integer from 2 to 8 and Z has the abovementioned meaning.

The 4-hydroxybenzyloxiranes of the formula II can be manufactured, for example, by oxidation of the corresponding olefines by means of percarboxylic acids, for example by means of perbenzoic acid. Another method of manufacture is the reaction of the corresponding alkali metal phenolates with 1-halogenopropene-2,3-oxides. Examples of suitable 4-hydroxybenzyloxiranes are 3-methyl-5-tert.-butyl-4-hydroxybenzyl-oxirane, 2-methyl-3,5-di-tert.-butyl-4-hydroxybenzyloxirane, 2-methyl-3,5-di-tert.-butyl-4-hydroxybenzyl-oxirane, 3,5-di-isopropyl-4-hydroxybenzyl-oxirane, 3-tert.-butyl-4-hydroxybenzyl-oxirane or 3,5-di-tert.-butyl-4-hydroxybenzyloxirane.

Preferably, those 4-hydroxybenzyloxiranes of the formula II are used in which $R_1$ and $R_2$ independently of one another represent an alkyl group with 1 to 8 carbon atoms, especially with 1 to 4 carbon atoms, and $R_3$ represents hydrogen. The use of 3,5-di-tert.-butyl-4-hydroxybenzyloxirane is particularly preferred.

The cyclic imides required as reactants are known compounds; they can contain one, two or three imide groups.

Examples of monoimides which can be used are the imides of succinic, glutaric, maleic and phthalic acid and of substituted phthalic acids, and also of uric acid, hydantoin and 5,5-dialkylhydantoins. Examples of cyclic diimides are: barbituric acid and its derivatives, uric acid, alloxane, dialuric acid, parabanic acid and alkylidene-bis-hydantoins. Amongst the technically accessible triimides, isocyanuric acid should be mentioned above all. Instead of isocyanuric acid, it is also possible to use cyanuric acid or a mixture of the two tautomers, since, under the reaction conditions, the derivatives of isocyanuric acid are produced from both compounds.

Preferably, the cyclic imide used is cyanuric acid, isocyanuric acid, an alkylidene-bis-hydantoin of the formula

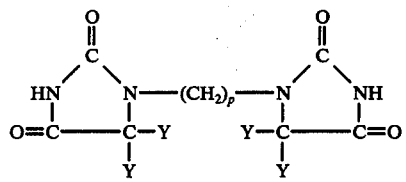

wherein Y denotes an alkyl radical with 1 to 4 carbon atoms and $p$ denotes an integer from 1 to 8, or an dialkylbarbituric acid of the formula

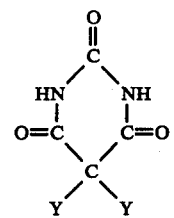

wherein Y has the abovementioned meaning.

Examples of these preferentially usable alkylidene-bis-hydantoins are: 5,5,5',5'-tetramethyl-1,1'-methylene-bis-hydantoin, 5,5,5',5'-tetramethyl-1,1'-tetramethylene-bis-hydantoin and 5,5,5',5'-tetramethyl-1,1'-octamethylene-bis-hydantoin. Examples of preferentially usable dialkylbarbituric acids are: 5,5-dimethylbarbituric acid or 5,5-diethylbarbituric acid.

The reaction of the oxiranes with the cyclic imides is in general carried out in stoichiometric ratios. It can be carried out without solvents, that is to say in the melt, or using a solvent. The reaction is preferably carried out in the presence of polar solvents, such as dimethylsulphoxide, dimethylformamide, dimethylacetamide or hexamethylphosphoric acid triamide.

The reaction is suitably carried out at a temperature between 100° and 250° C and at this temperature generally takes place sufficiently rapidly without a catalyst; it can, however, be further accelerated by catalysts. Suitable catalysts are aliphatic amines such as, for example, tri-isopropylamine or weak Lewis acids, such as, for example, lithium chloride or potassium chloride. The resulting compounds of the formula III can be isolated according to customary methods. If the reaction is carried out in a solvent, the products can be isolated from the solution, for example by evaporation or by dilution with water. The compounds of the formula III are crystalline and can therefore be purified by recrystallisation.

The compounds of the formula III obtained in this reaction can optionally be reacted further, in the sense of an esterification, with at least $m$ mols of a compound of the formula $R_5COZ$ or $(R_5CO)_2O$, wherein $R_5$ denotes an alkyl group with 1 to 17 carbon atoms, such as, for example, a methyl, ethyl, propyl, isobutyl, pentyl, undecyl or heptadecyl group, or the cyclohexyl or phenyl group, or a substituted phenyl group, for example a chlorophenyl, dichlorophenyl, hydroxyphenyl, tolyl, dimethylphenyl, tertiary butylphenyl, dodecylphenyl, dimethyl-hydroxyphenyl, di-tert.-butylhydroxyphenyl, methoxyphenyl, isopropoxyphenyl or octadecyloxyphenyl group or a benzyl or phenethyl group which can be substituted by alkyl and/or hydroxyl groups in the phenyl radical, for example a benzyl, phenethyl, hydroxybenzyl, di-isopropylhydroxybenzyl, di-tert.-butyl-hydroxyphenylethyl, dimethylbenzyl or n-butyl-phenylethyl group, and Z denotes halogen, —OH or -O-alkyl with 1 to 4 carbon atoms in the alkyl radical.

Preferably, compounds used for this purpose are compounds of the formula $R_5COZ$ or $(R_5CO)_2O$ in which $R_5$ denotes an alkyl group with 1 to 17 carbon atoms, a cyclohexyl group, a phenyl group, a phenyl group substituted by halogen, hydroxyl groups, alkyl groups with 1 to 4 carbon atoms or alkoxy groups with 1 to 18 carbon atoms, or a benzyl or phenethyl group substituted in the phenyl radical by one or two alkyl groups with 1 to 4 carbon atoms and/or a hydroxyl group, but especially compounds of the formula

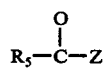

or $(R_5CO)_2O$, wherein $R_5$ denotes an alkyl group with 1 to 17 carbon atoms or a

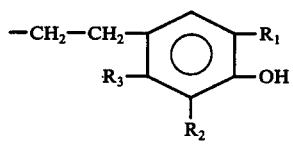

group in which $R_1$ and $R_2$ independently of one another represent an alkyl group with 1 to 4 carbon atoms, $R_3$ represents hydrogen and Z represents halogen.

Amongst the various compounds $R_5COZ$ which can be used for the esterification, important compounds are above all those in which Z represents a chlorine atom and $R_5$ has the abovementioned meaning. These are the carboxylic acid chlorides known as esterifying agents.

The compounds of the formula III in which $m = 1$ can, however, also be reacted with 0.5 mol of a dicarboxylic acid derivative of the formula

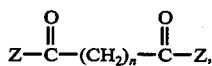

wherein $n$ denotes an integer from 2 to 8 and Z denotes halogen, —OH or O-alkyl with 1 to 4 carbon atoms in the alkyl radical. Examples of such compounds are succinic acid, adipic acid, sebacic acid or their halides or methyl or butyl esters. Preferably, compounds of the formula

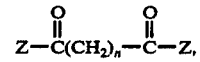

in which Z represents a halogen atom, especially a chlorine atom, and $n$ denotes an integer from 2 to 6, are used, for example succinic acid dichloride, adipic acid dichloride or sebacic acid dichloride.

The reaction of the compounds of the formula III with the reactants

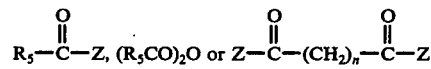

is carried out according to the known methods for the esterification of alcoholic hydroxyl groups; it can be carried out with or without the use of a solvent; a catalyst, or a hydrogen halide acceptor, can be used in addition. The choice of a solvent or of a catalyst and the choice of the reaction temperature depends on the particular reactants used; the working up also depends on the reactants. These methods for the esterification of alcoholic hydroxy compounds with carboxylic acids and their derivatives are generally sufficiently known as are the methods of isolation of the esterified reaction products.

The physical properties of the esterified reaction products depend on the nature of the esterification components Thus, compounds of the formula I in which $R_5$ is a long-chain alkyl radical, such as, for example, the stearic acid esters, are low-melting or oil-like substances. Compounds in which $R_5$ is a lower alkyl radical or an aryl radical, on the other hand, are high-melting crystalline substances.

The compounds according to the invention, of the formula I, are suitable for stabilising organic polymers against thermo-oxidative degradation. In addition, surprisingly, they are highly stable to the action of light or industrial waste gases.

The compounds according to the invention, of the formula I, in addition possess the advantage of extremely low volatility, especially if, in the formula I, $m = 2$ or 3 or if $m = 1$ and $R_4$ represents an acyl group

in which $R_5$ is a group of the formula

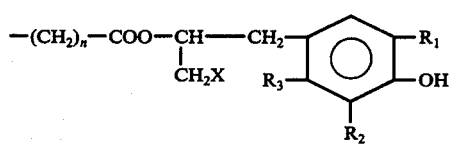

wherein $R_1$, $R_2$, $R_3$, X and $n$ have the initially mentioned meaning.

The organic polymers which can be stabilised in the sense of the present invention include, above all:

1. Polymers which are derived from hydrocarbons with single or double unsaturation, such as polyolefines, such as, for example, polyethylene, which can optionally be crosslinked, polypropylene, polyisobutylene, polymethylbutene-1, polymethylpentene-1, polybutene-1, polyisoprene, polybutadiene, polystyrene, polyisobutylene, copolymers of the monomers on which the homopolymers mentioned are based, such as ethylenepropylene copolymers, propylene-butene-1 copolymers, propyleneisobutylene copolymers, styrene-butadiene copolymers and terpolymers of ethylene and propylene with a diene, such as, for example, hexadiene, dicyclopentadiene or ethylidenenorbornene; mixtures of the abovementioned homopolymers such as, for example, mixtures of polypropylene and polyethylene, polypropylene and polybutene-1 or polypropylene and polyisobutylene.

2. Vinyl polymers containing halogen, such as polyvinyl chloride, polyvinylidene chloride and polyvinyl fluoride, but also polychloroprene and chlorinated rubbers.

3. Polymers which are derived from α,β-unsaturated acids and their derivatives, such as polyacrylates and polymethacrylates, polyacrylamides and polyacrylonitrile, as well as their copolymers with other vinyl compounds, such as acrylonitrile/butadiene/styrene, acrylonitrile/styrene and acrylonitrile/styrene/acrylic ester copolymers.

4. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinyl butyral, polyallyl phthalate, the polyallylmelamine and their copolymers with other vinyl compounds, such as ethylene/vinyl acetate copolymers.

5. Homopolymers and copolymers which are derived from epoxides, such as polyethylene oxide or the polymers which are derived from bis-glycidyl ethers.

6. Polyacetals, such as polyoxymethylene and polyoxyethylene, as well as those polyoxymethylenes which contain ethylene oxide as the comonomer.

7. Polyphenylene oxides.

8. Polyurethanes and polyureas.

9. Polycarbonates.

10. Polysulphones.

11. Polyamides and copolyamides which are derived from diamines and dicarboxylic acids and/or from aminocarboxylic acids or the corresponding lactams, such as polyamide 6, polyamide 6/6, and polyamide 6/10, polyamide 11 and polyamide 12.

12. Polyesters which are derived from dicarboxylic acids and dialcohols and/or from hydroxycarboxylic acids or the corresponding lactones, such as polyethylene glycol terephthalate, polybutylene terephthalate or poly-1,4-dimethylolcyclohexane terephthalate.

13. Crosslinked polymers which are derived from aldehydes on the one hand and phenols, ureas and melamines on the other, such as phenol-formaldehyde, urea-formaldehyde and melamine-formaldehyde resins.

14. Alkyd resins, such as glycerol-phthalic acid resins and their mixtures with melamine-formaldehyde resins.

15. Unsaturated polyester resins which are derived from copolyesters of saturated and unsaturated dicarboxylic acids with polyhydric alcohols, with vinyl compounds as cross-linking agents, and also their halogen-containing modifications of low inflammability.

16. Natural polymers such as cellulose, rubber, proteins and their polymer-homologously chemically modified derivatives, for example the cellulose ethers, such as methylcellulose.

To stabilise the said polymers, suitably 0.01 to 3% by weight of at least one compound of the formula I are used; preferably 0.1–1% by weight, based on the polymer, is used. Usually, the stabiliser is incorporated into the polymer by adding it to the hot melt of the polymer; it can, however, also be incorporated by adding it to the solution of the polymer or by adding it during the manufacture of the polymers.

To broaden the spectrum of action, other stabilisers can be added to the polymers in addition to the compounds of the formula I. These can be stabilisers which also counteract thermo-oxidative degradation or stabilisers which counteract purely thermal degradation or stabilisers which counteract photo-degradation. The compounds according to the invention are readily compatible with other stabilisers. Examples of such co-stabilisers are:

1. Antioxidants 1.1 Simple 2,6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-dioctadecyl-4-methylphenol.

1.2. Derivatives of alkylated hydroquinones, such as, for example, 2,5-di-tert.-butyl-hydroquinone, 2,5-di-tert.-amylhydroquinone, 2,6-di-tert.-butyl-hydroquinone, 2,5-di-tert.-butyl-4-hydroxy-anisole, 3,5-di-tert.-butyl-4-hydroxy-anisole, tris(3,5-di-tert.-butyl-4-hydroxyphenyl) phosphite, 3,5-di-tert.-butyl-4-hydroxyphenyl stearate and bis-(3,5-di-tert.-butyl-4-hydroxyphenyl) adipate.

1.3. Hydroxylated thiodiphenyl ethers, such as, for example, 2,2'-thio - bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxyphenyl)-disulphide.

1.4. Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butylphenol), 2,6-di-(3-tert.-butyl-5-methyl-2-hydroxybenzyl)-4-methylphenol, 2,2'-methylene-bis-[4-methyl-6-(α-methyl-cyclohexyl)-phenol], 1,1-bis-(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercapto-butane, 1,1,5,5-tetra-(5-tert.-butyl-4-hydroxy-2-methylphenyl)-pentane and ethylene glycol bis-[3,3-bis-(3'-tert.-butyl-4'-hydroxyphenyl)-butyrate].

1.5. O-, N- and S-benzyl compounds, such as, for example, 3,5,3',5'-tetra-tert.-butyl-4,4'-dihydroxydibenzyl ether, 4-hydroxy-3,5-dimethylbenzyl-mercaptoacetic acid octadecyl ester, tris-(3,5-di-tert.-butyl-4-hydroxybenzyl)-amine and bis-(4-tert.-butyl-3-hydroxy-2,6-dimethylbenzyl) dithioterephthalate.

1.6. Hydroxybenzylated malonic esters, such as, for example, 2,2-bis-(3,5-di-tert.-butyl-2-hydroxybenzyl)-malonic acid dioctadecyl ester, 2-(3-tert.-butyl-4-hydroxy-5-methylbenzyl)-malonic acid dioctadecyl ester, 2,2-bis-(3,5-di-tert.-butyl-4-hydroxybenzyl)-malonic acid didodecylmercaptoethyl ester and 2,2-bis-(3,5-di-tert.-butyl-4-hydroxybenzyl)-malonic acid di-[4-(1,1,3,3-tetramethylbutyl)-phenyl] ester.

1.7. Hydroxybenzyl-aromatics, such as, for example, 1,3,5-tri-(3,5-di-tert.-butyl-4-hydroxybenzyl)-2,4,6-trimethylbenzene, 1,4-di-(3,5-di-tert.-butyl-4-hydroxybenzyl)-2,3,5,6-tetramethylbenzene and 2,4,6-tri-(3,5-di-tert.-butyl-4-hydroxybenzyl)-phenol. 1.8. s-Triazine compounds, such as, for example, 2,4-bis-octylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxy-phenoxy)-s-triazine, 2,4,6-tris-(3,5-di-tert.-butyl-4-hydroxy-phenoxy)-s-triazine, 2,4,6-tris-(3,5-di-tert.-butyl-4-hydroxyphenylethyl)-s-triazine and 1,3,5-tris-(3,5-di-tert.-butyl-4-hydroxybenzyl)-isocyanurate.

1.9. Amides of β-(3,5-di-tert.-butyl-4-hydroxyphenyl)-propionic acid, such as, for example, 1,3,5-tris-(3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine.

1.10. Esters of β-(3,5-di-tert.-butyl-4-hydroxyphenyl)-propionic acid with monohydric or polyhydric alcohols such as, for example, with methanol, ethanol, octadecanol, 1,6-hexane-diol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethyl-isocyanurate and 4-hydroxymethyl-1-phospha-2,6,7-trioxabicyclo[2,2,2]-octane.

1.11. Esters of β-(5-tert.-butyl-4-hydroxy-3-methylphenyl)-propionic acid with monohydric or polyhydric alcohols such as, for example, with methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thia-undecanol, 3-thia-pentadecanol, trimethylhexanediol, trimethylolethane, trimethylolpropane, tris-hydroxyethylisocyanurate and 4-hydroxymethyl-1-phospha-2,6,7-trioxabicyclo[2,2,2]-octane.

1.12. Esters of 3,5-di-tert.-butyl-4-hydroxyphenylacetic acid with monohydric or polyhydric alcohols such as, for example, methanol, ethanol, octadecanol, 1,6-hexanediol, 1,9-nonanediol, ethylene glycol, 1,2-propanediol, diethylene glycol, thiodiethylene glycol, neopentyl glycol, pentaerythritol, 3-thiaundecanol, 3-thia-pentadecanol, trimethylhexanediol, trimethylolethane, trimethylolpropane, tris-hydroxyethylisocyanurate and 4-hydroxymethyl-1-phospha-2,6,7-trioxabicyclo[2,2,2]-octane.

1.13. Acylaminophenols, such as, for example, N-(3,5-di-tert.-butyl-4-hydroxyphenyl)-stearic acid amide and N,N'-di-(3,5-di-tert.-butyl-4-hydroxyphenyl)-thiobisacetamide.

1.14. Benzylphosphonates, such as, for example, 3,5-di-tert.-butyl-4-hydroxybenzyl-phosphonic acid dimethyl ester, 3,5-di-tert.-butyl-4-hydroxybenzyl-phosphonic acid diethyl ester, 3,5-di-tert.-butyl-4-hydroxybenzyl-phosphonic acid dioctadecyl ester and 5-tert.-butyl-4-hydroxy-3-methylbenzyl-phosphonic acid dioctadecyl ester.

1.15. Aminoaryl derivatives, such as, for example, phenyl-1-naphthylamine, phenyl-2-naphthylamine, N,N'-diphenyl-p-phenylenediamine, N,N'-di-2-naphthyl-p-phenylenediamine, N,N'-di-2-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and di-octyliminodibenzyl, polymerised 2,2,4-trimethyl-1,2-dihydroquinoline, octylated diphenylamine, nonylated diphenylamine, N-phenyl-N'-cyclohexyl-p-phenylenediamine, N-phenyl-N'-isopropyl-p-phenylenediamine, N,N'-di-sec.-octyl-p-phenylenediamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, diphenylamine-acetone condensation product, aldol-1-naphthylamine and phenothiazine.

2. UV-absorbers and light protection agents 2.1. 2-(2'-Hydroxyphenyl)-benztriazoles, such as, for example, the 5'-methyl-, 3',5'-di-tert.-butyl-, 5'-tert.-butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-α-methylbenzyl-5'-methyl-, 3'-α-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl- and 5-chloro-3',5'-di-tert.-amyl-derivative.

2.2. 2,4-bis-(2'-Hydroxyphenyl)-6-alkyl-s-triazines, such as, for example, the 6-ethyl-, 6-heptadecyl- and 6-undecylderivative.

2.3. 2-Hydroxybenzophenones, such as, for example, the 4-hydroxy-, 4-methoxy-, 4-octoxy-, 4-decyloxy-, 4-dodecyloxy-, 4-benzyloxy-, 4,2',4'-trihydroxy-, and 2'-hydroxy-4,4'-dimethoxy-derivative.

2.4. 1,3,bis-(2'-Hydroxybenzoyl)-benzenes, such as, for example, 1,3-bis-(2'-hydroxy-4'-hexyloxy-benzoyl)-benzene, 1,3-bis-(2'-hydroxy-4'-octyloxy-benzoyl)-benzene and 1,3-bis-(2'-hydroxy-4'-dodecyloxy-benzoyl)-benzene.

2.5. Esters of optionally substituted benzoic acids, such as, for example, phenyl salicylate, octylphenyl salicylate, dibenzoylresorcinol, bis-(4-tert.-butylbenzoyl)-resorcinol, benzoylresorcinol, 3,5-di-tert.-butyl-4-hydroxybenzoic acid 2,4-di-tert.-butylphenyl ester or octadecyl ester or 2-methyl-4,6-di-tert.-butylphenyl ester.

2.6. Acrylates, such as, for example, α-cyano-β,β-diphenylacrylic acid ethyl ester and isooctyl ester, α-carbomethoxycinnamic acid methyl ester, α-cyano-β-methyl-p-methoxycinnamic acid methyl ester and butyl ester and N-(β-carbomethoxyvinyl)-2-methylindoline.

2.7. Nickel compounds, such as, for example, nickel complexes of 2,2'-thio-bis[4-(1,1,3,3-tetramethylbutyl)-phenol], such as the 1:1 or the 1:2 complex, optionally with additional ligands such as n-butylamine, triethanolamine or N-cyclohexyldiethanolamine, nickel complexes of bis-[2-hydroxy-4-(1,1,3,3-tetramethylbutyl)-phenyl]-sulphone, such as the 2:1 complex, optionally with additional ligands such as 2-ethylcaproic acid, nickel dibutyldithiocarbamate, nickel salts of 4-hydroxy-3,5-di-tert.-butylbenzyl-phosphonic acid monoalkyl esters, such as of the methyl, ethyl or butyl ester, nickel complexes of ketoximes such as of 2-hydroxy-4-methylphenyl-undecyl ketonoxime, nickel 3,5-di-tert.-butyl-4-hydroxybenzoate and nickel isopropylxanthate.

2.8. Sterically hindered amines, such as, for example, 4-benzoyloxy-2,2,6,6-tetramethylpiperidine, 4-stearoyloxy-2,2,6,6-tetramethylpiperidine, bis-(2,2,6,6-tetramethylpiperidyl)-sebacate and 3-n-octyl-7,7,9,9-tetramethyl-1,3,8-triazaspiro[4,5]decane-2,4-dione.

2.9. Oxalic acid diamides, such as, for example, 4,4'-di-octyloxy-oxanilide, 2,2'-di-octyloxy-5,5'-di-tert.-butyl-oxanilide, 2,2'-di-dodecyloxy-5,5'-di-tert.-butyl oxanilide, 2-ethoxy-2'-ethyl-oxanilide, N,N'-bis-(3-dimethylaminopropyl)-oxalamide, 2-ethoxy-5-tert.-butyl-2'-ethyl-oxanilide and its mixture with 2-ethoxy-2'-ethyl-5,4'-di-tert.-butyl-oxanilide, and mixtures of ortho- and para-methoxy- and o- and p-ethoxydisubstituted oxanilides.

3. Metal deactivators, such as, for example, oxanilide, isophthalic acid dihydrazide, sebacic acid bis-phenylhydrazide, bis-benzylidene-oxalic acid dihydrazide, N,N'-diacetyladipic acid dihydrazide, N,N'-bis-salicyloyloxalic acid dihydrazide, N,N'-bis-salicyloylhydrazine, N,N'-bis-(3,5-di-tert.-butyl-4-hydroxyphenylpropionyl)-hydrazine, N-salicylal-N'-salicylidenehydrazine and 3-salicyloylamino-1,2,4-triazole.

4. Phosphites, such as, for example, triphenyl phosphite, diphenyl-alkyl phosphites, phenyl-dialkyl phosphites, tri-(nonylphenyl)-phosphite, trilauryl phosphite, trioctadecyl phosphite, 3,9-di-isodecyloxy-2,4,8,10-tetroxa-3,9-diphosphaspiro[5,5]undecane and tri-(4-hydroxy-3,5-di-tert.-butylphenyl)-phosphite.

5. Compounds which destroy peroxide, such as, for example, esters of β-thio-dipropionic acid, for example the lauryl, stearyl, myristyl or tridecyl ester, mercaptobenzimidazole and the zinc salt of 2-mercaptobenzimidazole.

6. Polyamide stabilisers, such as, for example, copper salts in combination with iodides and/or phosphorus compounds and salts of divalent manganese.

7. Basic co-stabilisers, such as, for example, melamine, benzoguanamine, polyvinylpyrrolidone, dicyandiamide, triallyl cyanurate, urea derivatives, hydrazine derivatives, amines, polyamides, polyurethanes, alkali metal and alkaline earth metal salts of higher fatty acids, for example Ca stearate, Zn stearate, Mg stearate, Na ricinoleate, K palmitate, antimony pyrocatecholate or tin pyrocatecholate.

8. PVC stabilisers, such as, for example, organic tin compounds, organic lead compounds and barium-cadmium salts of fatty acids.

9. Nucleating agents, such as, for example, 4-tert.-butyl-benzoic acid, adipic acid and diphenylacetic acid.

10. Urea derivatives, such as, for example, N-cyclohexyl-N'-1-naphthylurea, N-phenyl-N,N'-dicyclohexylurea, N-phenyl-N'-2-naphthylurea, N-phenylthiourea and N,N'-dibutylthiourea.

11. Other additives, such as, for example, plasticisers, lubricants, emulsifiers, fillers, carbon black, asbestos, kaolin, talc, glass fibres, pigments, optical brighteners, flameproofing agents and antistatic agents.

The polymer compositions stabilised in this way can be moulded by the customary methods, amongst which thermal methods such as extrusion, injection moulding, hot pressing, calendering and the like are of particular importance. The superiority of the compounds according to the invention manifests itself particularly with these thermal processing methods, in that no discolourations occur at the same time, and the compounds do not tend to sublime.

The invention is explained in more detail in the examples which follow. Therein, the parts are to be understood as parts by weight, unless expressly stated otherwise.

EXAMPLE 1

Manufacture of N-[2-hydroxy-3-(3-methyl-5-tert.-butyl-4-hydroxyphenyl)-propyl]-succinimide A solution of 6.6 g (0.03 mol) of 3-methyl-5-tert.-butyl-4-hydroxybenzyl-oxirane and 3 g (0.03 mol) of succinimide in 30 ml of dimethylformamide is stirred for 18 hours at a temperature of 150°-55° C whilst passing a slight stream of nitrogen through the mixture. After cooling to room temperature, the reaction mixture is poured into 150 ml of water and the oily reaction product which precipitates is dissolved in toluene. Successive extraction of the toluene phase with dilute hydrochloric acid, 5% strength aqueous sodium bicarbonate solution and water, drying over sodium sulphate and evaporation of the solvent gives the crude product. After recrystallisation from methylcellosolve, 6.5 g (68% of theory) of N-[2-hydroxy-3-(3-methyl-5-tert.-butyl-4-hydroxyphenyl)-propyl]-succinimide of melting point 217.5°-218° C are obtained in the form of colourless crystals.

EXAMPLES 2-5

The procedure in Example 1 is followed, but the starting components used are, on the one hand, 3,5-di-tert.-butyl-4-hydroxybenzyl-oxirane and, on the other, the particular equivalent amount of the cyclic imides listed in Table 1, column 2. The product obtained is indicated in column 4 and its melting point is indicated in column 5.

Table 1

| Example No. | Imide used | Molar ratio of oxirane:imide | Product obtained | Melting point (recrystallised from) |
|---|---|---|---|---|
| 2 | Succinimide | 1:1 | (structure) N-[2-Hydroxy-3-(3,5-di-tert.-butyl-4-hydroxyphenyl)-propyl]-succinimide | 134–35° C (ligroin/toluene) |
| 3 | Phthalimide | 1:1 | (structure) N-[2-Hydroxy-3-(3,5-di-tert.-butyl-4-hydroxyphenyl)-propyl]-phthalimide | 129–30° C (ligroin/toluene) |

Table 1-continued

| Example No. | Imide used | Molar ratio of oxirane:imide | Product obtained | Melting point (recrystallised from) |
|---|---|---|---|---|
| 4 | 5,5-Diethylbarbituric acid | 2:1 | 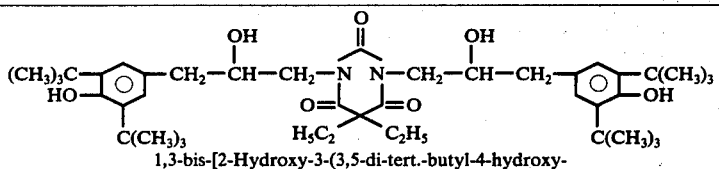<br>1,3-bis-[2-Hydroxy-3-(3,5-di-tert.-butyl-4-hydroxyphenyl)-propyl]-5,5-diethylbarbiturate | 148–49° C (ligroin/toluene) |
| 5 | 5,5,5',5'-tetramethyl-1,1'-methylene-bis-hydantoin | 2:1 | 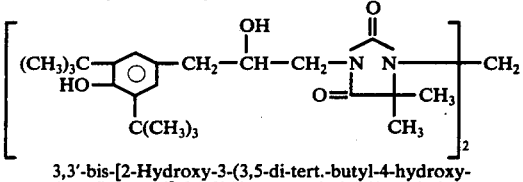<br>3,3'-bis-[2-Hydroxy-3-(3,5-di-tert.-butyl-4-hydroxyphenyl)-propyl]-5,5,5',5'-tetramethyl-1,1'-methylene-bis-hydantoin | 187–89° C (toluene) |

EXAMPLE 6

Manufacture of tris-[2-hydroxy-3-(3,5-di-tert.-butyl-4-hydroxyphenyl)-propyl]-isocyanurate A solution of 5.15 g (0.04 mol) of cyanuric acid and 34 g (0.13 mol) of 3,5-di-tert.-butyl-4-hydroxybenzyl-oxirane in 46 ml of dimethylformamide is stirred for 2.5 hours at 156° C whilst passing a stream of nitrogen through the mixture. After cooling to room temperature, the dark brown reaction solution is diluted with 200 ml of water and is repeatedly extracted with toluene. The combined extracts are repeatedly extracted with dilute hydrochloric acid, 5% strength aqueous sodium carbonate solution and water. Evaporation of the solvent gives a crude product which crystallises on treatment with a mixture of n-hexane and chloroform. Recrystallisation from ligroin/toluene gives 10 g (27% of theory) of tris-[2-hydroxy-3-(3,5-di-tert.-butyl-4-hydroxyphenyl)-propyl]-isocyanurate of melting point 206°–207° C in the form of colourless crystals.

EXAMPLE 7

Manufacture of 3-[2-hydroxy-3(3,5-di-tert.-butyl-4-hydroxyphenyl)-propyl]-5,5-dimethylhydantoin 25 mg of lithium chloride are added to 5.25 g (0.02 mol) of 3,5-di-tert.-butyl-4-hydroxybenzyl-oxirane and 2.56 g (0.02 mol) of 5,5-dimethylhydantoin and the mixture is kept at a melt at 220°–230° C for 60 minutes whilst stirring in a nitrogen atmosphere. After cooling, a glassy residue is obtained, which when recrystallised from toluene/isopropanol gives 6.2 g (78% of theory) of 3-[2-hydroxy-3-(3,5-di-tert.-butyl-4-hydroxyphenyl)-propyl]-5,5-dimethylhydantoin of melting point 175°–76° C in the form of colourless crystals.

EXAMPLE 8

Manufacture of 1,3-bis-[2-hydroxy-3-(3-methyl-5-tert.-butyl-4-hydroxyphenyl)-propyl]-5,5-diethylbarbiturate A solution of 11.0 g (0.05 mol) of 3-methyl-5-tert.-butyl-4-hydroxybenzyl-oxirane, 4.6 g (0.025 mol) of diethylbarbituric acid and 1 ml of triisopropylamine in 150 ml of dimethylformamide is stirred for 2 hours at 140°–50° C under nitrogen. Removal of the solvent in vacuo gives a resinous residue which after treatment with dilute hydrochloric acid and recrystallisation from ligroin/isopropanol consists of crude bis-[2-hydroxy-3-(3-methyl-5-tert.-butyl-4-hydroxyphenyl)-propyl]-5,5-diethylbarbiturate. A further recrystallisation from ligroin/toluene gives the pure product of melting point 147°–48° C in the form of colourless crystals.

EXAMPLE 8a

If in the above example, instead of 3-methyl-5-tert.-butyl-4-hydroxybenzyl-oxirane, the equivalent amount of 3,5-diisopropyl-4-hydroxybenzyl-oxirane is used, 1,3-bis[2-hydroxy-3-(3,5-diisopropyl-4-hydroxyphenyl)-propyl]-5,5-diethylbarbiturate is obtained, which melts at 126°–127° C after recrystallisation from hexane/benzene.

EXAMPLE 9

Manufacture of tris-[2-acetoxy-3-(3,5-di-tert.-butyl-4-hydroxyphenyl)-propyl]-isocyanurate 1.9 g (2.17 mmols) of tris-[2-hydroxy-3-(3,5-di-tert.-butyl-4-hydroxyphenyl)-propyl]-isocyanurate and 5 ml of acetic anhydride are heated for 1 hour to the reflux temperature and after cooling to room temperature the mixture is poured onto ice. After working up, a colourless oil is obtained which, when recrystallised from alcohol, gives 2.0 g (93% of theory) of tris-[2-acetoxy-3-(3,5-di-tert.-butyl-4-hydroxyphenyl)-propyl]-isocyanurate of melting point 143°–45° C in the form of colourless crystals.

EXAMPLE 10

Manufacture of 1,3-bis-[2-stearoyloxy-3-(3,5-di-tert.-butyl-4-hydroxyphenyl)-propyl]-5,5-diethylbarbiturate 7.0 g (0.01 mol) of 1,3-bis-[2-hydroxy-3-(3,5-di-tert.-butyl-4-hydroxyphenyl)-propyl]-5,5-diethylbarbiturate and 6 g (0.02 mol) of stearic acid chloride in 50 ml of ligroin are brought to the reflux temperature and the resulting clear solution is kept at this temperature until the evolution of hydrochloric acid has ceased. After evaporating the solvent in vacuo, a syrupy residue is obtained which when chromatographed on a silica gel column gives 6.5 g (53% of theory) of 1,3-bis-[2-stearoyloxy-3-(3,5-di-tert.-butyl-4-hydroxyphenyl)-propyl]-5,5-diethylbarbiturate as an almost colourless oil.

EXAMPLES 11 and 12

The procedure under Example 7 is followed but in one case the product of Example 3 is reacted with adipic acid chloride in the molar ratio of 2:1 whilst in the other case the product of Example 2 is reacted with γ-(3,5-di-tert.-butyl-4-hydroxyphenyl)-propionic acid chloride in the molar ratio of 1:1. The compounds 11 and 12, thus obtained, are listed in Table 2.

employed. The incipient easily visible crumbling of the test strip is defined as the end point.

Table 3

| Stabiliser from Example No. | Days to reach incipient decomposition | |
|---|---|---|
| | 149° C | 135° C |
| None | <1 | ~3 |
| 10 | 15 | 166 |
| 12 | 16 | 103 |
| 4 | 40 | 183 |
| 6 | 34 | 125 |
| 8 | 29 | 119 |
| 5 | 38 | 141 |
| 8a | 14 | 75 |
| 9 | 44 | 177 |
| 11 | 31 | 90 |

Table 2

| No. | Formula and name | Melting point (recrystallised from) |
|---|---|---|
| 11 | 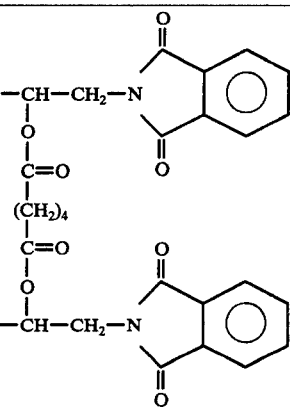 Adipate of N-[2-hydroxy-3-(3,5-di-tert.-butyl-4-hydroxyphenyl)-propyl]-phthalimide | 194 – 95° C (ethyl acetate) |
| 12 | 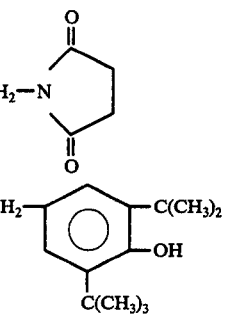 N-[2-(γ-3,5-Di-tert.-butyl-4-hydroxyphenyl)-propionoxy-3-(3,5-di-tert.-butyl-4-hydroxyphenyl)-propyl]-succinimide | 139 – 40° C (ligroin) |

EXAMPLE 13

100 parts of polypropylene (melt index 3.2 g/10 minutes, 230° C/2,160 g) are thoroughly mixed for 10 minutes in a shaking apparatus with 0.2 part of one of the additives listed in Table 3 below. The resulting mixture is kneaded for 10 minutes in a Brabender plastograph at 200° C and the mixture thus obtained is subsequently pressed in a sheet press at 260° C platen temperature to give 1 mm thick sheets from which strips 1 cm wide and 17 cm long are punched.

The activity of the additives added to the test strips is tested by heat aging in a circulating air oven at 135° C and 149° C, using an additive-free test strip for comparison. For this test, 3 test strips of each formulation are

EXAMPLE 14

100 parts of polypropylene (melt index 3.2 g/10 minutes, 230° C/2,160 g) are thoroughly mixed for 10 minutes in a shaking apparatus with 0.1 part of one of the additives listed in Table 4 below and 0.3 part of dilaurylthiodipropionate.

The resulting mixture is kneaded for 10 minutes in a Brabender plastograph at 200° C and the mixture thus obtained is subsequently pressed in a sheet press at 260° C platen temperature to give 1 mm thick sheets from which strips 1 cm wide and 17 cm long are punched.

The activity of the additives added to the test strips is tested by heat aging in a circulating air oven at 135° C and 149° C, using a test strip which only contains 0.3 part of dilaurylthiodipropionate for comparison. For this test, three test strips of each formulation are employed. The incipient easily visible crumbling of the test strip is defined as the end point.

Table 4

| Stabiliser from Example No. | Days to reach incipient decomposition | |
|---|---|---|
| | 149° C | 135° C |
| Comparison | 5 | 11 |
| 4 | 50 | 210 |
| 8 | 49 | 166 |
| 9 | 65 | 207 |
| 5 | 41 | 144 |
| 6 | 40 | 148 |
| 8a | 37 | 131 |
| 10 | 47 | 166 |
| 11 | 55 | 167 |
| 12 | 21 | 110 |

EXAMPLE 15

The test specimens described in Example 13 were also tested for their colour stability, namely:

a. after incorporation (Table 5 column 2)
b. after 500 hours exposure in a Xenotest apparatus of Messrs. Hanau (Table 5, column 3)
c. after 1 week's treatment with boiling water (Table 5, column 4)

For Table 5, an empirical colour scale was used, in which 5 denotes colourless, 4 denotes a just perceptible slight discolouration and 3, 2, 1 and < 1 denote progressively stronger discolouration.

Table 5

| Stabiliser from Example No. | Colour rating according to scale 1–5 | | |
|---|---|---|---|
| | After incorporation | After exposure to light | Boiling water, 1 week |
| 12 | 4–5 | 5 | 4–5 |
| 4 | 5 | 5 | 5 |
| 6 | 5 | 5 | 4–5 |
| 10 | 4–5 | 5 | 5 |
| 8 | 5 | 5 | 4–5 |
| 5 | 4–5 | 5 | 5 |
| 8a | 4–5 | 5 | 4–5 |
| 9 | 4–5 | 5 | 4 |
| 11 | 5 | 5 | 4–5 |

EXAMPLE 16

The test specimens described in Example 14 were also tested for their colour stability, namely:

a. after incorporation (Table 6, column 2)
b. after 500 hours exposure in a Xenotest apparatus of Messrs. Hanau (Table 6, column 3)
c. after 1 week's treatment with boiling water (Table 6, column 4)

For Table 6, an empirical colour scale was used, in which 5 denotes colourless, 4 denotes a just perceptible slight discolouration and 3, 2, 1 and < 1 denote progressively stronger discolouration.

Table 6

| Stabiliser from Example No. | Colour rating according to scale 1–5 | | |
|---|---|---|---|
| | After incorporation | After exposure to light | Boiling water, 1 week |
| 4 | 5 | 5 | 5 |
| 5 | 4–5 | 5 | 4–5 |
| 6 | 5 | 5 | 4–5 |
| 8 | 5 | 5 | 4–5 |
| 8a | 5 | 5 | 4–5 |
| 9 | 5 | 5 | 4–5 |
| 10 | 5 | 5 | 5 |
| 11 | 5 | 4–5 | 5 |
| 12 | 5 | 5 | 4–5 |

EXAMPLE 17

100 parts of polypropylene (melt index 19 g/10 minutes, 230° C/2,160 g) are thoroughly mixed for 10 minutes in a shaking apparatus with 0.1 part of a stabiliser obtained according to Example 4 or Example 6.

The resulting mixture is extruded in a laboratory single-screw extruder ("Plamvo") at 260° C nozzle temperature, 100 r.p.m. and a throughput of 50 g/minute, and is subsequently granulated.

The resulting granules are spun in a spinning apparatus at a nozzle temperature of 280° C to give polyfilaments which are then additionally stretched in the ratio of 1:5.5.

The resulting filaments are subjected to a "gas-fading test" based on Standard AATCC, test method 23-1957, and consisting of exposing the test specimens to the waste gases from a butane gas burner at 60° C for 24 hours.

The visual colour assessment shows in both cases that the test specimens have remained colourless.

EXAMPLE 18

Shavings (chips) 25μ thick are cut by means of a microtome from the 1 mm test sheets described in Example 13. These chips are clamped between stainless steel grids and the sample carriers thus obtained are suspended in a circulating air oven and aged at 135° C or 147° C. The time after which, on gently tapping the grid, degraded polypropylene drops out in the form of a powder is defined as the end point (a check is carried out 1–2× daily). The results are quoted in hours (Table 7).

Table 7

| Stabiliser from Example No. | Hours to reach incipient decomposition | |
|---|---|---|
| | at 147° C | at 135° C |
| Without additive | 10 | 20 |
| 10 | 90 | 310 |
| 12 | 40 | 140 |
| 4 | 120 | 360 |
| 6 | 330 | 910 |
| 8 | 140 | 360 |
| 5 | 140 | 480 |
| 8a | 35 | 140 |
| 9 | 400 | 1,120 |
| 11 | 90 | 240 |

EXAMPLE 19

Shavings (chips) 25μ thick are cut by means of a microtome from the 1 mm test sheets described in Example 14. These chips are clamped between stainless steel grids and the sample carriers thus obtained are suspended in a circulating air oven and aged at 135° C or 147° C. The time after which, on gently tapping the grid, degraded polypropylene drops out in the form of a powder is defined as the end point (a check is carried out 1–2× daily). The results are quoted in hours (Table 8).

Table 8

| Stabiliser from Example No. | Hours to reach incipient decomposition | |
|---|---|---|
| | at 147° C | at 135° C |
| Comparison | 10 | 20 |
| 4 | 120 | 360 |
| 8 | 140 | 360 |
| 9 | 400 | 1,120 |
| 5 | 160 | 480 |
| 6 | 260 | 910 |

Table 8-continued

| Stabiliser from Example No. | Hours to reach incipient decomposition | |
|---|---|---|
| | at 147° C | at 135° C |
| 8a | 70 | 260 |
| 10 | 140 | 480 |
| 11 | 160 | 380 |
| 12 | 70 | 190 |

What we claim is:
1. A compound of the formula

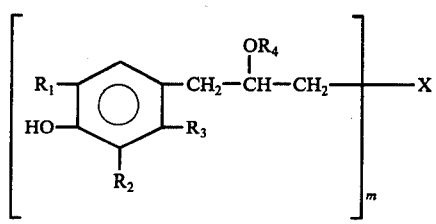

wherein $m$ is an integer from 1 to 2 and $R_1$ denotes an alkyl group with 1 to 8 carbon atoms, a cycloalkyl group with 6 to 8 carbon atoms or an aralkyl group with 7 to 9 carbon atoms, $R_2$ denotes hydrogen, an alkyl group with 1 to 8 carbon atoms, cycloalkyl group with 6 to 8 carbon atoms or an aralkyl group with 7 to 9 carbon atoms, $R_3$ denotes hydrogen or a methyl group, $R_4$ denotes hydrogen or a $$-\overset{O}{\underset{\|}{C}}-R_5$$

group, $R_5$, if $m$ is 1 or 2, is an alkyl group with 1 to 17 carbon atoms, a cyclohexyl group, a phenyl group or phenyl substituted by halogen, hydroxyl groups, alkyl groups with 1 to 4 carbon atoms or alkoxy groups with 1 to 18 carbon atoms or an aralkyl group which can be substituted by alkyl and/or hydroxyl groups in the aromatic radical, and, if $m$ is 1, is a group

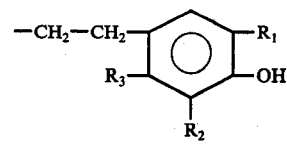

X is selected from the group consisting of hydantoin, 5,5-dimethylhydantoin, and alkylene-bis-hydantoin, said hydantoin being bonded to the rest of the molecules via the nitrogen in position 3, and $n$ denotes an integer from 2 to 8.

2. A compound of claim 1, wherein $R_1$ and $R_2$ independently of one another are alkyl groups with 1 to 8 carbon atoms, $R_3$ is hydrogen, $R_4$ is hydrogen or $$-\overset{O}{\underset{\|}{C}}-R_5$$

group, $R_5$, if $m$ is 1 or 2, is an alkyl group with 1 to 17 carbon atoms, a cyclohexyl group, a phenyl group, a phenyl group substituted by halogen, hydroxyl groups, alkyl groups with 1 to 4 carbon atoms or alkoxy groups with 1 to 18 carbon atoms, or a benzyl or phenethyl group substituted in the phenyl radical by one or two alkyl groups with 1 to 4 carbon atoms and/or a hydroxy group, or, if $m$ is 1, is a group

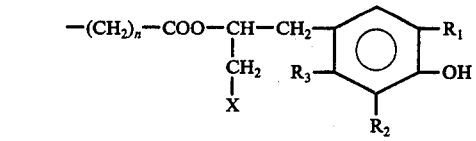

3. A compound of claim 1, wherein $R_1$ and $R_2$ independently of one another are alkyl groups with 1 to 4 carbon atoms, $R_3$ is hydrogen, $R_4$ is hydrogen or a

group, $R_5$, if $m$ is 1 or 2, is an alkyl group with 1 to 17 carbon atoms or a group

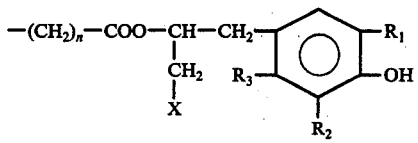

if $m = 1$, is a group

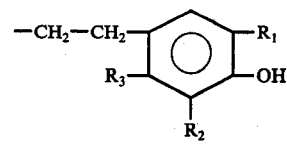

and $n$ is an integer from 2 to 6.

4. A compound of claim 1, wherein $R_1$ and $R_2$ independently of one another are alkyl groups with 1 to 4 carbon atoms and $R_3$ and $R_4$ are hydrogen.

5. A compound of claim 1, wherein $m$ is 2, $R_1$ and $R_2$ each is a tertiary butyl group, $R_3$ and $R_4$ are hydrogen, X is a group

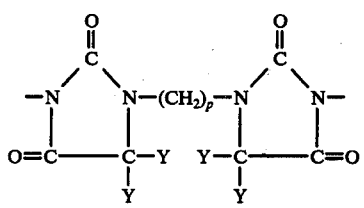

where
Y is an alkyl group with 1 to 4 carbon atoms and $p$ is an integer from 1 to 8.

6. The compound of claim 1 of the formula

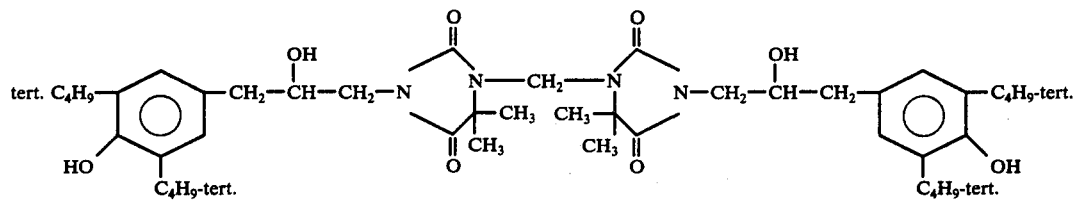
7. An organic polymeric composition stablized against degradation with 0.01 to 3.0 percent by weight of a compound of claim 1.
8. A composition according to claim 7 wherein the organic polymer is a polyolefin.
9. A composition according to claim 7 wherein the polymer is polypropylene.
10. A polyolefin composition stablized with 0.01 to 3.0 percent by weight of the compound of claim 6.
* * * * *